US010245169B2

(12) United States Patent
Hiernaux et al.

(10) Patent No.: US 10,245,169 B2
(45) Date of Patent: Apr. 2, 2019

(54) ASSEMBLY FOR SECURING GASTROINTESTINAL TISSUE FOLDS

(71) Applicant: ENDO TOOLS THERAPEUTICS S.A., Gosselies (BE)

(72) Inventors: Martin Hiernaux, Brussels (BE); Alexandre Chau, Ixelles (BE); Michel Joie, Ernage (BE)

(73) Assignee: ENDO TOOLS THERAPEUTICS S.A., Gosselies (BE)

( * ) Notice: Subject to any disclaimer, the term of this patent is extended or adjusted under 35 U.S.C. 154(b) by 324 days.

(21) Appl. No.: 15/311,717

(22) PCT Filed: Jun. 16, 2015

(86) PCT No.: PCT/EP2015/063480
§ 371 (c)(1),
(2) Date: Nov. 16, 2016

(87) PCT Pub. No.: WO2015/193317
PCT Pub. Date: Dec. 23, 2015

(65) Prior Publication Data
US 2017/0095363 A1    Apr. 6, 2017

(30) Foreign Application Priority Data

Jun. 20, 2014 (EP) .................................. 14173296

(51) Int. Cl.
*A61F 5/00* (2006.01)
*A61B 17/04* (2006.01)
(Continued)

(52) U.S. Cl.
CPC ........ *A61F 5/0086* (2013.01); *A61B 17/0401* (2013.01); *A61B 17/0469* (2013.01);
(Continued)

(58) Field of Classification Search
CPC ...... A61B 17/0487; A61B 2017/00818; A61B 2017/0409; A61B 2017/0414;
(Continued)

(56) References Cited

U.S. PATENT DOCUMENTS 7,390,332 B2 *  6/2008  Selvitelli ............ A61B 17/0401
                                                                606/144
7,416,554 B2 *  8/2008  Lam .................. A61B 17/00234
                                                                606/153
(Continued)

FOREIGN PATENT DOCUMENTS

EP     1 568 326 A1    8/2005
WO     01/39671 A1     6/2001
WO     02/36020 A1     5/2002

OTHER PUBLICATIONS

International Search Report from the European Parent Office in International Application No. PCT/EP2015/063480 dated Sep. 16, 2015.

*Primary Examiner* — Ryan J. Severson
(74) *Attorney, Agent, or Firm* — The Marbury Law Group, PLLC

(57) ABSTRACT

Assembly for endoscopically securing gastrointestinal tissue folds, comprising a first tissue anchor and a second tissue anchor, a first suture thread part and a second suture thread part, each of the first and second thread parts having a connected end and a free end opposite the connected end. The first thread part and the second thread part are tied to each other through a sliding knot, such that the first thread part firms a post of the sliding knot along which the sliding knot is arranged to slide during tightening of the assembly and such that the second thread part wraps around the post to create the sliding knot. The first thread part extends from the first anchor to past the sliding knot where the first thread part's free end forms a post free end, and the second thread
(Continued)

part extends from the second anchor to past the sliding knot where the second thread part's free end is free, such that the sliding knot is interposed between the first and second anchors. The first or the second anchor comprises a knot retaining through hole, wherein the post free end slidingly passes through the knot retaining through hole, the knot retaining through hole having a size preventing the sliding knot to pass through the knot retaining through hole, such that the anchor can be used as a knot retainer during tightening.

18 Claims, 14 Drawing Sheets

(51) Int. Cl.
    *A61B 17/06*         (2006.01)
    *A61B 17/00*         (2006.01)

(52) U.S. Cl.
    CPC ............... *A61B 2017/00818* (2013.01); *A61B 2017/0409* (2013.01); *A61B 2017/0414* (2013.01); *A61B 2017/0417* (2013.01); *A61B 2017/0445* (2013.01); *A61B 2017/0464* (2013.01); *A61B 2017/0474* (2013.01); *A61B 2017/0475* (2013.01); *A61B 2017/06052* (2013.01)

(58) Field of Classification Search
    CPC .... A61B 2017/0438; A61B 2017/0445; A61B 2017/0446; A61B 2017/0458; A61B 2017/0459; A61B 2017/0462; A61B 2017/0475; A61B 2017/0477; A61B 2017/0488; A61B 2017/0496; A61F 5/0086
    See application file for complete search history.

(56) References Cited

U.S. PATENT DOCUMENTS

| | | | | |
|---|---|---|---|---|
| 7,651,509 B2* | 1/2010 | Bojarski | ............ | A61B 17/0401 606/139 |
| 7,887,551 B2* | 2/2011 | Bojarski | ............ | A61B 17/0401 606/139 |
| 7,909,851 B2* | 3/2011 | Stone | ................ | A61B 17/0401 606/232 |
| 8,216,260 B2* | 7/2012 | Lam | ................ | A61B 17/00234 606/153 |
| 8,366,744 B2* | 2/2013 | Bojarski | ............ | A61B 17/0401 606/232 |
| 8,540,740 B2* | 9/2013 | Lam | ................ | A61B 17/00234 606/153 |
| 8,551,118 B2* | 10/2013 | Zeiner | ................ | A61B 17/0401 606/139 |
| 8,623,051 B2* | 1/2014 | Bojarski | ............ | A61B 17/0401 24/129 R |
| 8,696,704 B2* | 4/2014 | Selvitelli | ............ | A61B 17/0401 606/232 |
| 8,790,369 B2* | 7/2014 | Orphanos | .......... | A61B 17/0401 606/232 |
| 9,173,653 B2* | 11/2015 | Bojarski | ............ | A61B 17/0401 |
| 9,220,494 B2* | 12/2015 | Bojarski | ............ | A61B 17/0401 |
| 9,421,012 B2* | 8/2016 | Orphanos | .......... | A61B 17/0401 |
| 9,439,643 B2* | 9/2016 | Darois | ................ | A61B 17/0057 |
| 9,517,060 B2* | 12/2016 | Flint | .................. | A61B 17/0401 |
| 2002/0019649 A1* | 2/2002 | Sikora | ................ | A61B 17/0401 606/232 |
| 2003/0130694 A1* | 7/2003 | Bojarski | ............ | A61B 17/0401 606/228 |
| 2004/0122456 A1* | 6/2004 | Saadat | ............ | A61B 17/00234 606/157 |
| 2004/0138683 A1 | 7/2004 | Shelton et al. | | |
| 2004/0147958 A1* | 7/2004 | Lam | .................. | A61B 17/00234 606/232 |
| 2005/0075654 A1* | 4/2005 | Kelleher | ............ | A61B 17/0401 606/151 |
| 2005/0187577 A1* | 8/2005 | Selvitelli | ............ | A61B 17/0401 606/232 |
| 2005/0251205 A1* | 11/2005 | Ewers | ................ | A61B 17/0401 606/232 |
| 2005/0251208 A1* | 11/2005 | Elmer | ................ | A61B 17/0401 606/232 |
| 2006/0142784 A1 | 6/2006 | Kontos | | |
| 2006/0190042 A1 | 8/2006 | Stone et al. | | |
| 2006/0293709 A1* | 12/2006 | Bojarski | ............ | A61B 17/0401 606/232 |
| 2007/0083236 A1* | 4/2007 | Sikora | ................ | A61B 17/0401 606/232 |
| 2008/0140093 A1 | 6/2008 | Stone et al. | | |
| 2008/0188893 A1* | 8/2008 | Selvitelli | ............ | A61B 17/0401 606/232 |
| 2009/0018552 A1* | 1/2009 | Lam | .................. | A61B 17/00234 606/139 |
| 2009/0024144 A1* | 1/2009 | Zeiner | ................ | A61B 17/0401 606/142 |
| 2009/0024148 A1* | 1/2009 | Zeiner | ................ | A61B 17/0401 606/151 |
| 2009/0024163 A1* | 1/2009 | Zeiner | ................ | A61B 17/0401 606/232 |
| 2009/0275980 A1* | 11/2009 | Zeiner | ................ | A61B 17/0401 606/232 |
| 2010/0114162 A1* | 5/2010 | Bojarski | ............ | A61B 17/0401 606/228 |
| 2011/0022061 A1* | 1/2011 | Orphanos | .......... | A61B 17/0401 606/139 |
| 2011/0288584 A1* | 11/2011 | Bojarski | ............ | A61B 17/0401 606/232 |
| 2011/0306989 A1 | 12/2011 | Darois et al. | | |
| 2012/0277775 A1* | 11/2012 | Lam | .................. | A61B 17/00234 606/153 |
| 2014/0088644 A1* | 3/2014 | Flint | .................. | A61B 17/0401 606/230 |
| 2014/0114353 A1* | 4/2014 | Bojarski | ............ | A61B 17/0401 606/232 |
| 2014/0296913 A1* | 10/2014 | Orphanos | .......... | A61B 17/0401 606/232 |
| 2016/0120536 A1* | 5/2016 | Bojarski | ............ | A61B 17/0401 606/232 |
| 2017/0095363 A1* | 4/2017 | Hiernaux | ............ | A61B 17/0401 |

* cited by examiner

ASSEMBLY FOR SECURING GASTROINTESTINAL TISSUE FOLDS

RELATED APPLICATIONS

This application is the U.S. national phase entry under 35 U.S.C. § 371 of PCT Application No. PCT/EP2015/063480, filed Jun. 16, 2015 which claims the priority benefit of European Patent Application No. EP 14173296 filed Jun. 20, 2014. Applications PCT/EP2015/063480 and EP 14173296 are incorporated herein by reference in their entirety.

The present invention is related to anchor systems for securing endoscopically made tissue folds, in particular gastrointestinal tissue folds, such as tissue folds created for stomach reduction.

One method for treating obesity involves reducing the distensibility and volume of the stomach. This can be performed endoscopically through known procedures, which consist in making a fold in the wall of the stomach and fixing the fold by a suture thread. Alternatively, a plurality of folds can be made, which are pulled towards one another thereby obtaining a larger volume and distensibility reduction by closing off a space in between the folds. Tissue anchor systems for use with suture threads have been developed for fixing the folds.

Tissue anchor systems of the above kind are known from U.S. Pat. No. 8,257,394, which describes in relation to FIGS. 11A and 12A-G a number of tissue anchor configurations. All these configurations comprise a pair of anchor tags which are connected through a thread. The thread is passed as a loop through the pair of anchors and a knot is made proximally of the most proximal anchor, in order to prevent release of the anchor from the thread. For fixing the tissue fold, the proximal anchor and the knot are pushed towards the fold, by a knot pusher, while maintaining one limb of the thread loop under tension. When the knot has been pushed to a desired location, which corresponds to the anchors being placed tightly at opposite sides of the fold, the knot is secured by appropriate tensioning of the other limb of the thread.

Other anchor configurations are described in U.S. Pat. No. 8,343,175 in relation to FIGS. 7-15. FIGS. 7-14 of the latter document describe configurations wherein one anchor is provided with special means for avoiding sliding of the thread and hence release of the anchor and in some cases wherein the thread itself is formed in a particular manner for co-operation with the sliding avoiding means. These systems are however difficult to implement in the small dimensions (on the order of magnitude of a few mm) that anchors for minimally invasive interventions must have, FIGS. 15A-C describe anchor systems wherein the anchors are secured by a knot, similar to U.S. Pat. No. 8.257,394.

Suture anchor configurations are also used for repairing tissue lesions, such as following minimally invasive interventions. U.S. Published Patent Application No. 2006/0142784 and U.S. Published Patent Application No. 2006/0190042 describe assemblies comprising a pair of tissue anchors connected through a suture thread forming a sliding knot for maintaining the tissue anchors connected to one another.

The knot-secured anchor configurations of the prior art described above have the advantage of simplicity. Furthermore, they can rely on a large number of laparoscopic or arthroscopic knots that have purposely been developed and widely tested to date.

A drawback of the above described knot-secured anchor systems is that tightening and hence the final securement of the system is difficult to control. While testing anchor systems of the above kind, the inventors have often observed that during securement of the anchor, additional undesired knots formed between the knot and the proximal anchor due to prompt twisting of the thread limbs. More particularly, referring by way of example to FIG. 12 A of U.S. Pat. No. 8,257,394, the inventors have often observed that anchor 244 displaces from knot 258, and during securement of the knot, the thread limbs passing through anchor 244 at holes 248 and 246 get twisted at one or both sides of the anchor 244 and create one or more additional, uncontrollable knots. The uncontrolled knots and twists can prevent the knot 258 to slide along the thread limb 94 and/or can prevent the proximal anchor tag 244 to move closer to the distal anchor tag 242. In those cases, proper tightening of the folds cannot be achieved.

In addition, it has been observed that the distal anchor may make multiple turns on itself hence twisting thread limbs, which increases friction between the thread limbs hindering sliding of the thread 94 along the anchor tag 242 and hence proper securing of the knot. Furthermore, the thread is passed twice through each anchor tag, as e.g. through hole pairs 246, 248 and 250, 252 of the anchor tags of FIG. 12A of U.S. Pat. No. 8,257,394. It has been observed that when the thread gets twisted, which is often the case, the anchor acts as a backpack strap adjuster and it becomes hard to slide the thread along the distal anchor tag during tightening the knot. It therefore becomes very hard to balance out the lengths of the two thread limbs between the anchors. This leads to situations in which one thread limb may be under tension, whereas the other one is not. This may have a deleterious effect on the securement of the knot, since sliding knots require that both thread limbs be maintained under tension in order to keep the knot secured. In some cases, the force required for sliding the thread through the distal anchor and tighten the assembly is larger than the strength of the thread or the anchor itself, leading to rupture.

Moreover, since the above operations must be performed within small endoluminal space, the visual guidance by an endoscope camera is limited, and often the surgeon can only see the knot but not the anchor, or the thread limbs distal of the knot. Therefore, the surgeon cannot see what happens distally of the knot, where threads and/or the anchor may twist without being noticed.

The above problems lead to anchor systems which are poorly secured and which may loosen after some time.

It is therefore an object of the invention to provide knot-secured tissue anchor assemblies for endoscopic use, which provide improved reliability in securing the tissue folds and reduce risk of relaxation of the anchor system. It is an object to provide such tissue anchor assemblies, in which the securing operation of the anchor assembly is easier to control compared to prior art assemblies. It is an object to provide tissue anchor assemblies which are easier to manufacture and easier to work with.

According to aspects of the invention, there is therefore provided an assembly for securing gastrointestinal tissue folds as set out in the appended claims. The assembly comprises a first tissue anchor and a second tissue anchor, and a first suture thread part and a second suture thread part, each of the first and second suture thread parts having a connected end and a free end opposite the connected end. The first thread part and the second thread part are tied to each other through a sliding knot. In the sliding knot, the first thread part forms a post of the knot along which the sliding knot is arranged to slide during tightening of the assembly and the second thread part wraps around the post to create the sliding knot, i.e. the second thread part acts as a loop limb of the sliding knot. The assembly is configured to be tightened by sliding the knot along the post, such as in the direction of the first anchor.

According to an aspect of the invention, the first thread part extends from the first anchor to past the sliding knot where the first thread part's free end forms a post free end, and the second thread part extends from the second anchor to past the sliding knot where the second thread part's free end is free, such that the sliding knot is interposed between the first and second anchors. Hence, the first and second thread parts form a thread path extending between the first anchor and the second anchor, and the sliding knot is located on this (portion of) thread path. From a surgeon's point of view, the first anchor can act as a distal anchor and the second anchor can act as a proximal anchor. The knot is then located distally of the proximal(most) anchor, and proximally of the distal(most) anchor.

According to a second aspect of the invention, the second anchor (i.e. the proximalmost anchor) comprises an advantageously transverse through hole. The through hole has a size preventing the sliding knot to pass through it. However, the post free end slidingly passes through the through hole. By so doing it is obtained that the second anchor can be used as a knot retainer during tightening or tensioning the sliding knot.

Alternatively, the through hole can be provided in the first anchor with same functionality. In this case, the first anchor will act as proximalmost anchor.

According to a still alternative second aspect of the invention, the assembly comprises an endoscopic knot tightening instrument and a grasping or engagement device. The endoscopic knot tightening instrument is of tubular shape with a distal open end arranged for abutment against the proximalmost tissue anchor (the second anchor, or possibly the first anchor). The grasping device is arranged for being slidingly accommodated inside the knot tightening instrument. The endoscopic knot tightening instrument comprises a slit extending longitudinally along an outer wall of the endoscopic knot tightening instrument. The slit is open to the distal end and has a width sized such that the post free end (the first thread part's free end) can pass through the slit and preventing the sliding knot to pass through the slit.

With any of the above second aspects it is obtained that twisting of thread limbs around the proximal tag is greatly reduced such that the knot can be slid more easily along the post. There is hence much less possibility that the proximal anchor gets trapped in twisting thread limbs. This kind of twisting (γ) is described further below in relation to FIGS. 11-12. It has been observed that present aspect eliminates or at least greatly reduces such twisting. It is hence obtained that assemblies according to the invention can be tightened with greater ease and tightening control is improved.

An additional advantage is that the proximal anchor remains accessible to any pusher or tightening instrument, and remains visible to an endoscopic camera during tightening of the sliding knot, since the sliding knot remains distally of the proximal anchor.

According to a third aspect of the invention, the connected ends of the first and second thread parts are secured to the corresponding anchors. In other words, the connected ends of the thread parts are fastened to the corresponding anchor such that the anchor cannot slide along the thread part in at least one direction.

According to an alternative third aspect of the invention, the connected ends of the first and second thread parts are attached to each other thereby forming a thread loop. The thread loop is closed by the sliding knot. The loop slidingly passes through the first and second anchors such that the anchors can advantageously pivot on the loop without twisting the loop (i.e. twisting thread limbs of the loop on each other).

With either configuration of the second aspect, both thread parts can be maintained under tension during use, and a reliable securement of the knot and the entire assembly is obtained.

Above aspects of the invention can be combined to obtain synergistic advantages. It has been observed that the above configurations reduce undesired twisting of thread limbs on one another. And even if any such twisting occurs, the ability of reliably securing the anchor assembly can still be maintained. This is explained further below in relation to FIGS. 11-16. Without wishing to be bound by theory, it is believed that this is due to a synergistic combination of two effects. The sliding knot being located in the thread path between the two anchors reduces possible twisting between the proximal anchor and the knot, which in turn facilitates knot sliding along the post. In addition, both above configurations, with either a single thread path, or a double thread path (loop) between the two anchors ensure that the thread limbs constituting the knot remain under tension during use. Still additionally, either the through hole (retaining the knot) or the knot tightening instrument allow improved control in tightening the knot. As a result, a reliable anchor is obtained.

Sliding knots used in assemblies according to aspects of the invention are advantageously unidirectional sliding knots, which allow movement (slip) of the knot in only one direction along the post, i.e. the knot slides along the post in a direction of reducing the thread length between the anchors, but not in the opposite sense or direction due to locking of the knot when both threads are under tension. Sliding knots that can be used in aspects of the invention are non locking or ratchet sliding knots.

Further advantageous aspects of the present invention are set out in the dependent claims.

Methods of securing gastrointestinal tissue folds are also described.

Aspects of the invention will now be described in more detail with reference to the appended drawings, which are illustrative only and wherein same reference numbers indicate same features, wherein:

FIG. 15 represents a plan view of the anchor assembly 40 before tightening, whereas

FIGS. 17-19 represent different embodiments for the, hook retaining tag.

Figure 1:
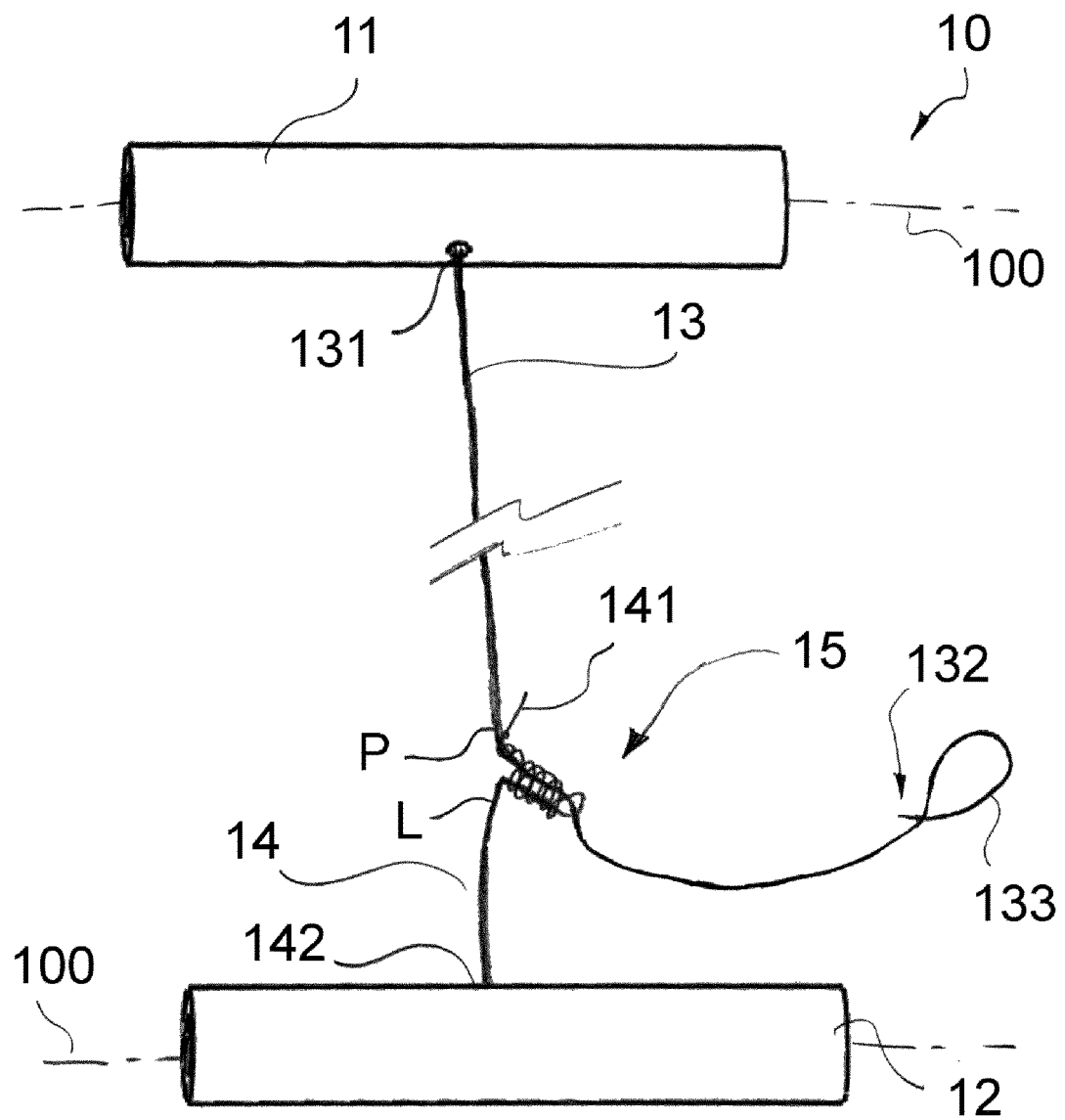
FIG. 1 represents a perspective view of a tissue anchor assembly according to aspects of the invention.

A sliding knot as used herein refers to a knot wherein the knot can slide along one of the thread limbs, referred to as the post. Sliding knots are also referred to as slip knots. They are generally obtained by wrapping the other thread limb, referred to as the loop limb (wrapping limb or non-post), around the post limb. In some knots, the post and loop limbs can alternate during tying of the knot. In the present description, the post limb refers to the thread limb along which the knot can be slid. Sliding knots used in the present invention are advantageously sliding knots used in laparoscopic surgery, and possibly in arthroscopic surgery.

Many different kinds of sliding knots can be used in anchor assemblies according to the present invention, including but not limited to (referred to with their common name): the Nicky's knot, the Tennessee slider knot, the Roeder knot, the modified Roeder knot, the 4S knot or 4S modified Roeder knot, the Mishra's knot, the Duncan loop, the modified taut line hitch, the hangman's knot, the Prusik knot. Some of these knots are described by:

Ian K. Y. Lo in "Arthroscopic Knots: Determining the Optimal Balance of Loop Security and Knot Security", Arthroscopy: The Journal of Arthroscopic and Related Surgery, Vol 20, No 5 (May-June), 2004: pp 489-502— see in particular FIG. 1 A-D, and H. T. Sharp and J. H. Dorsey in "The 4-S modification of the Roeder knot: How to tie it", Obstetrics & Gynecology, vol. 90, No. 6, December 1997, pp. 1004-1006 (4S modified Roeder knot).

These knots are commonly referred to as non locking sliding knots or sometimes ratchet knots. Non locking sliding knots are opposed to locking or self locking sliding knots, such as the SMC knot, the modified Tennessee slider knot or the Giant knot which can securely lock into place by modifying their shape subsequently to an action on the post limb, the loop limb or both. Locking sliding knots are more difficult to use as the action required to lock them in place is difficult to perform in an endoscopic environment.

Advantageously, non locking sliding knots used in the present invention allow movement along the post in one direction only, provided the loop limb is under (minimal) tension. Advantageously, attempts to move the knot in the opposite direction along the post when both thread limbs are under tension, will lock the knot. Due to the pressure of the tissue acting on both limbs of the knot, the knot will remain secured in place. Advantageously, non locking sliding knots have an appropriate knot security (i.e. they will not slip on the post) without the need to perform additional operations in order to finally secure the knot in place after tightening the anchor assembly, such as by making additional reverse half hitches on alternating posts (RHAP) once the knot has been slid into place. Placing additional RHAP is challenging in an endoscopic environment. It has been shown that the 4S modified Roeder knot or 4S knot offers good knot security without the need to add additional RHAPs (see Howard T. Sharp et al in "A simple modification to add strength to the Roeder knot", The Journal of the American Association of Gynecologic Laparoscopists, February 1996, Vol. 3, No. 2, pp. 305-307).

In describing the present invention, the terms distal and proximal are used according to the customary practice in the field of endoluminal or minimally invasive surgery. Therefore, the term distal as used herein refers to a direction away from, or at an opposite end of the location where the surgeon operates a medical device, such as an endoscope to tighten the knot of anchor assemblies of the invention. The term proximal as used herein refers to a direction towards or closer to the location where the surgeon operates the medical device as stated above.

A first example of anchor assembly according to aspects of the invention is represented in FIG. 1. Anchor assembly 10 comprises a distal anchor 11 and a proximal anchor 12. Anchors 11 and 12 are advantageously of elongate shape, i.e. with a dimension along a longitudinal axis 100 being significantly larger than dimensions in a plane perpendicular to the longitudinal axis 100. Anchors 11 and 12 are advantageously of cylindrical shape, with the length of the cylinder (along axis 100) being advantageously larger than its diameter. Other suitable shapes, such as disc-shaped can however be contemplated. As will be further described, at least proximal anchor 12 is advantageously tubular, with an internal lumen 123 (FIG. 2) running longitudinally.

A suture thread 13 has a distal end 131 tied or otherwise secured to the distal anchor 11. Another suture thread 14 has a proximal end 142 tied or otherwise secured to the proximal anchor 12. Threads 13 and 14 are advantageously tied or secured to the corresponding anchor 11 and 12 respectively at a centre or in a median plane of the anchor. By way of example, in FIG. 1, the threads 13 and 14 are tied to the corresponding anchor at about half way the length of the anchor, corresponding to a median sectional plane of the cylinder. Thread 13 can be secured to the distal anchor 11 and thread 14 can be secured to the proximal anchor 12 according to known techniques, such as by gluing to the anchor, by fusing the thread to the anchor (in case of thermoplastic materials), or by a knot preventing the thread to slide out of a hole provided through the anchor (unidirectional securement). Advantageously, threads 13 and 14 are secured to the corresponding anchor while enabling the anchor to be pivoted on the respective thread, advantageously without twisting the thread, i.e. the threads are so attached to prevent motion longitudinally along the respective thread, while allowing rotation/pivoting on the thread.

The two threads 13 and 14 are tied to each other with a sliding knot 15. Sliding knot 15 is arranged in proximity of the distal end 141 of thread 14, which ends freely (without further attachment or loading) after having formed the loop limb L of sliding knot 15. Thread 13 forms the post P of sliding knot 15 and further extends past knot 15 to its proximal end 132.

Thread 13 advantageously forms a loop 133 at its proximal end 132, which facilitates grabbing and pulling the post limb during tightening of the knot and reduces the risk of thread rupture at the location where it is grabbed.

Knot 15 is advantageously shown in the Figures to be a 4-S modification of the Roeder knot, as described by H. T. Sharp and J. H. Dorsey in "The 4-S modification of the Roeder knot: How to tie it", Obstetrics & Gynecology, vol. 90, No. 6, December 1997, pp. 1004-1006. However, other kinds of knots as described above can be used. The 4-S modified Roeder knot is tied by starting with a single flat throw of the two threads 13 and 14, followed by wrapping the loop limb L (14) around the post limb P (13) four times. The loop limb L is then passed over the post limb P, from anterior to posterior to form a half-hitch, followed by passing the loop limb L from posterior to anterior around the post limb P to complete a square knot. It will be convenient to note that in the Figures, the knot is in some cases represented schematically and not in full detail.

The 4-S modified Roeder knot is a sliding knot which allows movement of the knot along the post limb P in only one direction, namely towards the distal end 131 of the thread 13. With minimal tension on the loop limb L, movement along the post limb P in the opposite direction, namely towards the proximal end 132 of the thread 13 is prevented.

Figure 2:
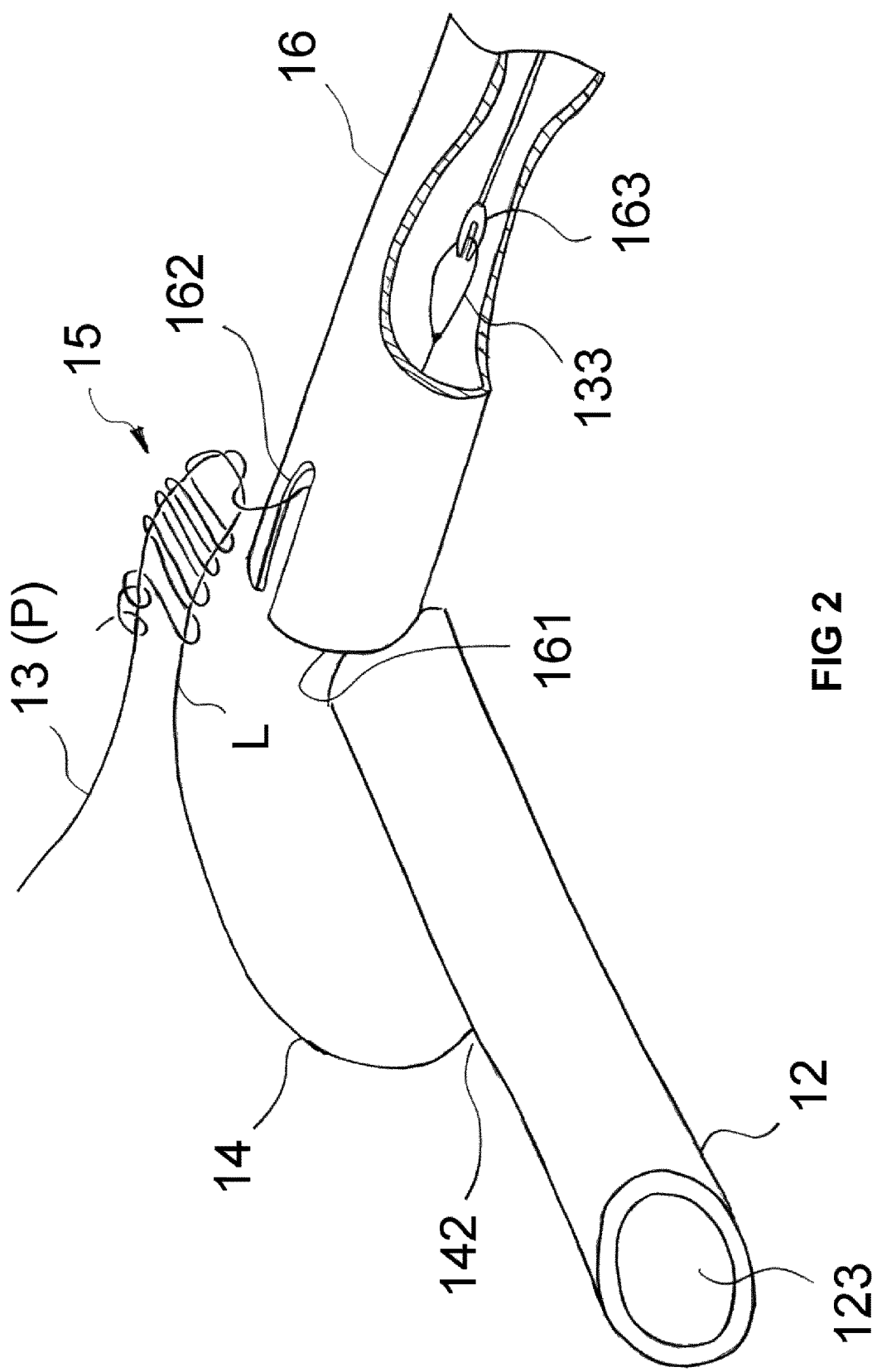
FIG. 2 represents a perspective view of a knot tightening instrument for use with the assembly of FIG. 1.

Once the assembly 10 has been introduced and positioned in the body, as will be described later, with the distal anchor 11 located at a distal side of a tissue fold, or even of a sequence of tissue folds, and with the proximal anchor 12 located at a proximal side of the fold, the knot 15 can be tightened and secured. To this end, use can be made of an endoscopic knot tightening instrument 16 as shown in FIG. 2. Instrument 16 is of tubular shape with advantageously a distal open end 161.

A grasping device 163 is slidingly arranged at the inside of tubular instrument 16 as shown in the cut out portion of instrument 16 in FIG. 2. Before instrument 16 is made to abut against anchor 12, grasper 163 is pushed to exit from instrument 16 past the distal end 161 to grab the loop 133 of the post limb of knot 15 and pull it inside instrument 16. Instrument 16 further comprises a slit 162 extending longitudinally along the outer wall. Slit 162 is open to the distal end 161 and has a width sized such that thread 13 (the post P) can pass through, but preventing the knot 15 to pass through slit 162.

Hence, during pulling loop 133 inside instrument 16 by grasper 163, instrument 16 can be turned on its longitudinal axis so that thread 13 is caught in slit 162. Thereafter, thread 133 is further pulled proximally inside instrument 16 by grasper 163. By so doing, knot 15 will arrive at slit 162, but is prevented to pass through. Since knot 15 is a sliding knot, further pulling the thread 13 (i.e. the post limb P) down the instrument 16 will make knot 15, and particularly the loop limb L (thread 14) slide along the post limb to reduce the thread length between the anchors 11 and 12 and hence tighten the threads 13 and 14 between the knot 15 and the respective anchors 11 and 12. Since knot 15 does not allow a back movement along the post limb P, the knot 15 is secured through the tension on the threads and the anchor assembly remains tightened when the proximal end of thread 13 (loop 133) is released.

The loop 133 may be made discernibly different as compared to the remainder portion of thread 13, 14 in order to be easily recognised by the endoscope camera. Hence, the loop 133 may have a different colour, be made of a different material, or have other kinds of recognizable features, such as visual markers, which the remainder portion of thread does not have.

It will be convenient to note that in this particular example, the portion of thread 14 extending between the proximal anchor 12 and the knot 15 is advantageously made as small as possible in order to avoid tension relaxation when releasing the free end 132 of thread 13 from the grasper 163.

It has been observed that no twisting of the threads 13 or 14 on themselves occurs, or only a few twists, which will not affect the tightening procedure, so that the anchor can be secured with more ease and improved reliability.

Figure 3:
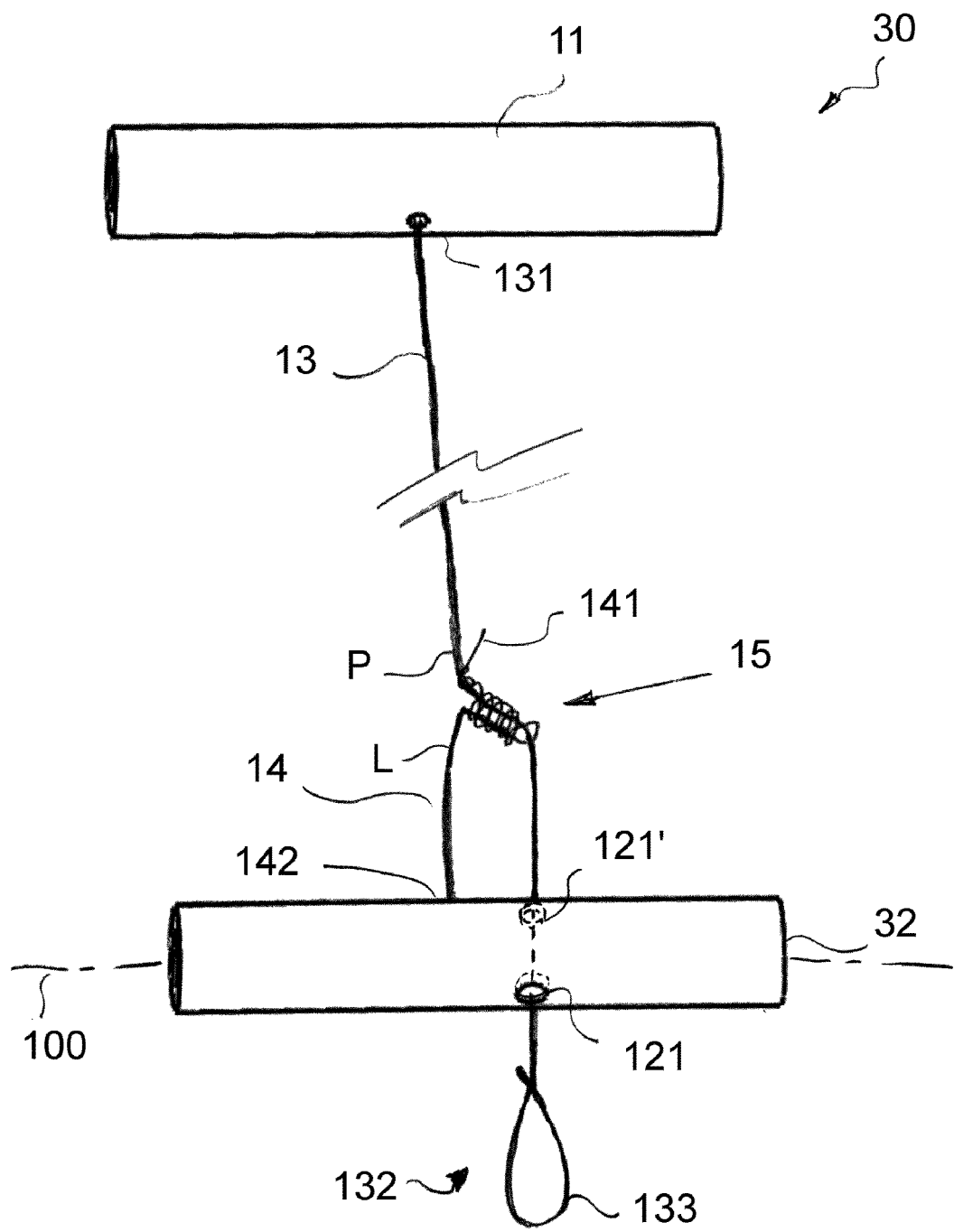
FIG. 3 represents a perspective view of another tissue anchor assembly according to aspects of the invention.

FIG. 3 shows an anchor assembly 30 according to aspects of the invention, which is slightly modified compared to assembly 10. Assembly 30 only differs from assembly 10 in that the proximal anchor 32 comprises a through hole 121-121'. Through hole 121 is oriented in a transverse direction of anchor 12, cross to a longitudinal axis 100. Advantageously, through hole 121 is oriented such that it has an axis perpendicular to the longitudinal axis 100 and advantageously intersecting the longitudinal axis 100, such that a plane formed by both axes corresponds to a plane in which thread 14 is located when the assembly 30 is tensioned.

It will be convenient to note that proximal anchor 12, 32 is typically made hollow or tubular for reasons that will be described later. Therefore, in practice, through hole 121 will be formed of a pair of holes 121, 121' arranged at opposite sides of the anchor 32, each of the holes 121, 121' running through the anchor wall and communicating through the internal lumen of anchor 32.

Through hole 121, 121' has a size allowing thread 13 to pass through, more particularly allowing the part extending from the knot 15 to the free end 132 of the thread 13 to pass through hole 121. Thread 13 is made to pass through hole 121 from a distal side (hole 121'), where thread 14 is located, to a proximal side (hole 121), opposite the distal side. However, the size of through hole 121, 121' is small enough preventing knot 15 to pass through it. As a result, when one pulls on the end 132 of thread 13 through the hole 121, the knot 15 is made to remain at the distal side of anchor 32. Through hole 121 therefore has a same function as the slit 162 of the knot tightening instrument 16 of FIG. 2.

In this regard, the size of each hole of the pair of holes 121 need not be the same. By way of example, distal hole 121' can have a smaller size than proximal hole 121. As a result the size of distal hole 121' advantageously prevents knot 15 to pass through, and the size of proximal hole 121 may be made somewhat larger. Additionally, the size of proximal hole 121 may have a size preventing end loop 133 to pass through. This avoids that during placement of the anchors, the thread end 132 or loop 133 would accidentally slip back out of the hole 121 and 121' towards the distal side (towards the knot side).

An advantage of through hole 121, 121' is therefore that no specific instrument as the one depicted in FIG. 2 is required for tightening the knot 15. It suffices to use an endoscopic tube rigid enough for pushing against the proximal anchor and in which a grasper 163 is arranged for pulling on the proximal end of the post limb thread 13. It has also been observed that the through hole 121 enables to further reduce undesired thread twisting in assembly 30 compared to assembly 10 when the endoscopic tube is maintained against anchor 32 whilst tightening.

It will be convenient to note that the through hole 121, 121' can alternatively be provided through anchor 11 instead of anchor 32. Anchor 11 will in this case act as proximal anchor.

Figure 4:
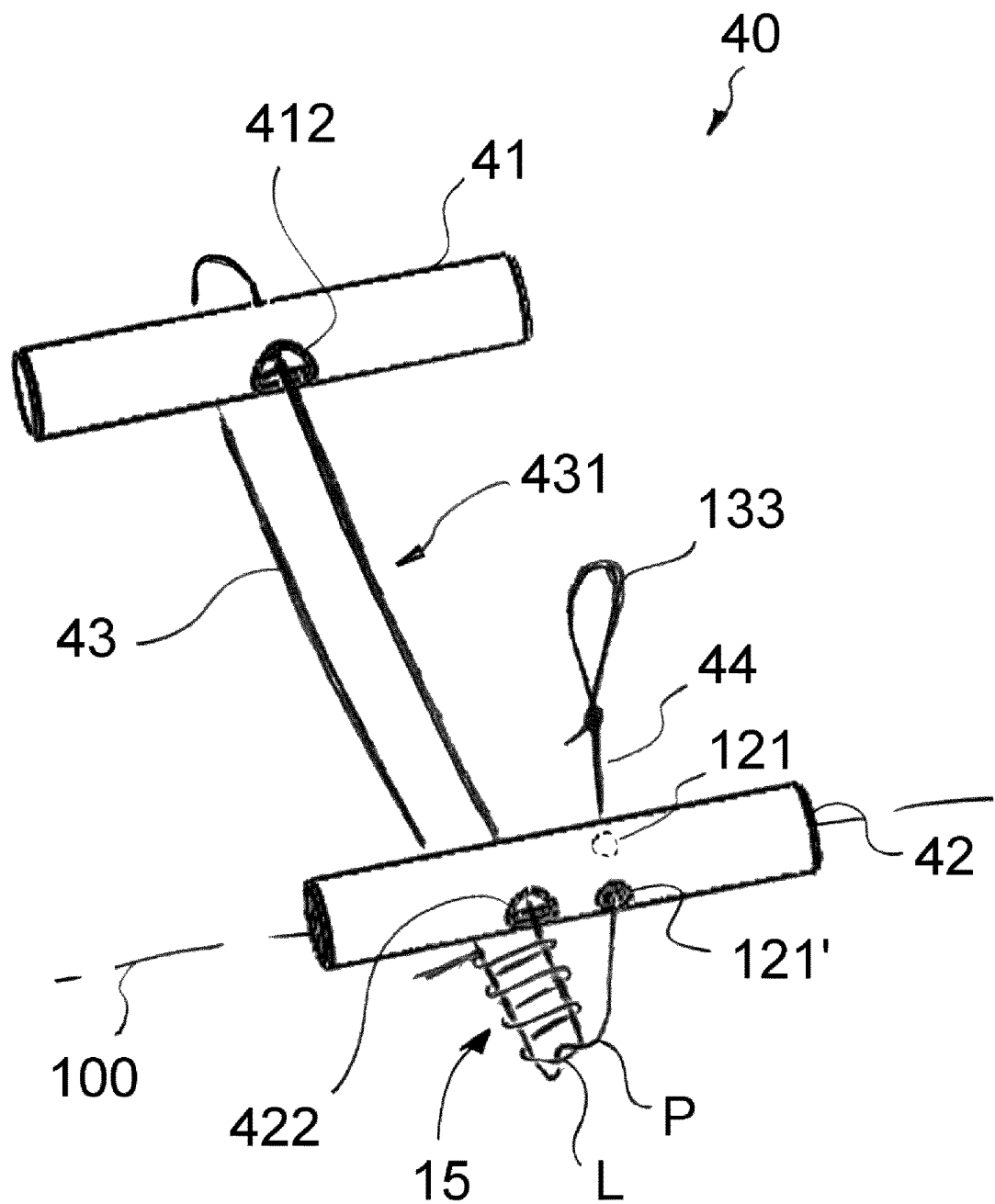
FIG. 4 represents a perspective view of yet another tissue anchor assembly according to aspects of the invention.

Yet another anchor assembly according to aspects of the invention is shown in FIG. 4. Anchor assembly 40 differs from anchor assembly 30 in that the threads 13 and 14 now form a single thread 43, which is passed once through distal anchor 41 and once through proximal anchor 42 to form a loop 431. The loop 431 is closed by sliding knot 15, which is identical to the knots of assemblies 10 and 30. Knot 15 is formed by wrapping one limb of thread 43 (the loop limb L) on the other limb of thread 43 (the post limb P). Forming a loop 431 increases the tensioning force that can be applied between the anchors, since each limb of the loop can accept half of the overall tension.

The free end 44 of the post limb P of thread 43 is passed through through holes 121', 121, similarly to assembly 30. It will be convenient to note that the proximal anchor 42 is represented in FIG. 4 from a different view as the anchors in FIG. 3. That is, when the anchor assembly 40 will be tightened, proximal anchor 42 will be turned 90° about longitudinal axis 100 such that the axis defining through hole 121-121' is oriented perpendicularly to the orientation of the thread 43 in loop 431. Same applies to anchor 41.

Anchors 41 and 42 each comprise a through hole 412, 422 respectively, for passing thread 43 through. Similarly to through hole 121, in case either one or both anchors are tubular, either one or both through holes 412 and 422 can be formed of a pair of oppositely arranged holes (not shown) through the wall of the tubular anchor, communicating through the internal lumen of the anchor. The anchors 41 and 42 therefore are arranged along the loop 431 of thread 43 formed by knot 15. There is no need to further secure the anchors to thread 43, so that anchors 41 and 42 are suspended by thread 43 inside loop 431, and attached but not secured to the thread, so that they are able to slide along thread 43.

Advantageously, either one or both distal anchor 41 and proximal anchor 42 are pivotally attached to loop 431, i.e. either one or both anchors can pivot on the thread of loop 431, advantageously without causing twisting of the loop. This can be obtained by loop 431 passing through the distal anchor 41, and advantageously also through the proximal anchor 42 only once, i.e. loop 431 passes through one through hole 412 only in the distal anchor 41 and through one through hole 422 only in the proximal anchor 42. It has been observed that when the thread is made to pass only once through distal anchor, it makes thread 43 slide easier along through hole 412 compared to when thread 43 would pass a second time through anchor 41, in the opposite direction (as e.g. the case in FIG. 12A of U.S. Pat. No. 8,257,394). In the latter case, there is a substantial risk that the anchor acts as a backpack strap adjuster relative to the thread of loop 431, which would prevent the loop thread from sliding freely through the anchor. This is required during tightening in order to balance the lengths of both limbs of loop 431 between the anchors. It has been observed that when thread 43 gets twisted, which is often the case, the fact of having a double passage through the distal anchor as in the prior art makes it hard to slide thread 43 along distal anchor 41 during tightening the knot 15. If the anchors are prevented to slide along loop 431 during tightening, which would be the case when the anchor would act as a backpack strap adjuster, one limb of loop 431 may become under tension, whereas the other may not. This reduces the maximal strength before rupture of the anchor assembly. A single passage as in FIG. 4 significantly reduces this drawback.

It will be convenient to note that the through hole 121, 121' can be omitted in assembly 40. The knot 15 can then be tightened analogously to assembly 10. It will also be convenient to note that the through hole 121, 121' can alternatively be provided through anchor 41 instead of anchor 42. Anchor 41 will in this case act as proximal anchor.

Figure 5:
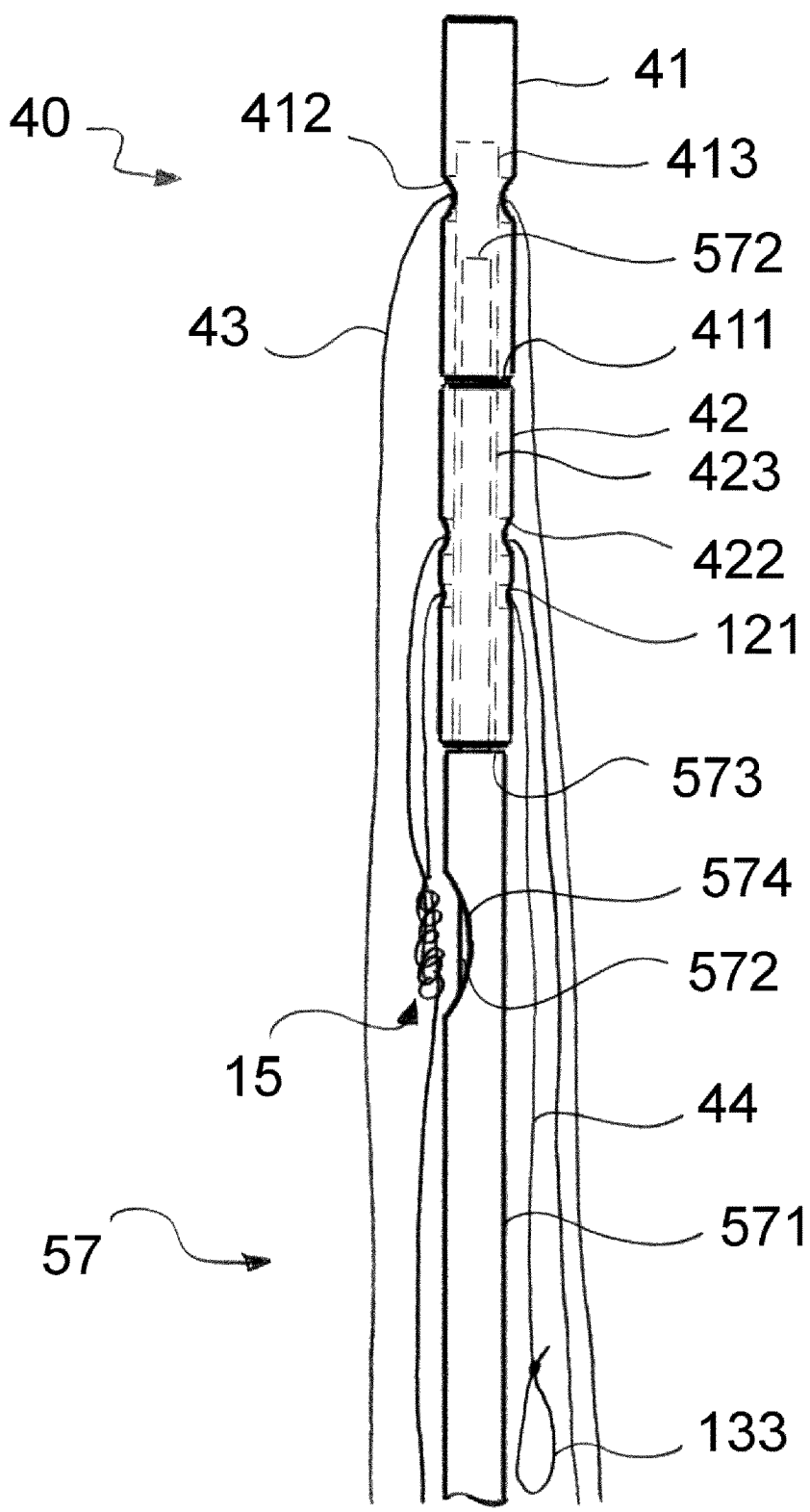
FIG. 5 represents a side view of a pusher assembly with the anchor assembly of FIG. 4 mounted on it.
Figure 6:
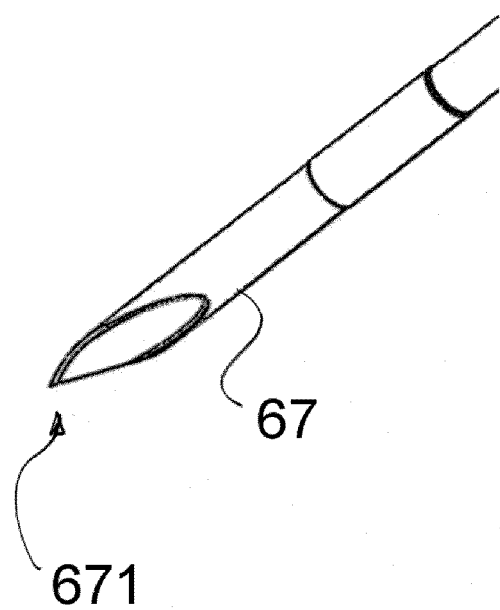
FIG. 6 represents a perspective view of a needle in which the pusher assembly of FIG. 5 is slidingly held.

The placement of the anchor assembly through a tissue fold will now be described referring to FIGS. 5-9. The anchor assembly 40 is first assembled outside the patient. Thread 43 is passed through the anchors 41, 42. Sliding knot 15 is tied, and the free end 44 is drawn through the through hole 121 (assemblies 30 and 40). Next, as shown in FIG. 5, the anchor assembly is mounted on a push rod assembly 57. Push rod assembly 57 comprises an outer push tube 571 and an inner push rod 572 slidingly arranged inside push tube 571. Inner push rod 572 is made to project from push tube 571. The proximal anchor 42, which is tubular with axial lumen 423, is slid over push rod 572 until it abuts against a distal end 573 of push tube 571. Advantageously, the internal axial lumen of proximal anchor 42 is of sufficiently larger cross size than the cross size of push rod 572, so that the anchor 42 is arranged with sufficient play around push rod 572. Distal anchor 41 may comprise an advantageously axial blind hole 413 receiving push rod 572, such that anchors 41 and 42 will be aligned on push rod 572 when mounted. The thread 43 and knot 15 is left to hang loose from the anchors, along the push rod assembly 57. Alternatively, a recess, groove or slit 574 can be provided along the push tube to accommodate the thread 43 and the knot 15.

The anchor assembly 40 and push rod assembly 57 so mounted are then inserted in a hollow suture needle 67 (FIG. 6), so that the distal anchor 41 will be the first one to exit needle 67 from the distal opening 671 when the assembly 40+57 is pushed from the proximal side in distal direction up the needle 67. Needle 67, with assembly 40+57 arranged in it, is then introduced in the patient. It will be convenient to note that the knot 15 is introduced in the patient together with the anchors, and is not slid from outside the patient to the inside after placement of the anchors.

Figure 7:
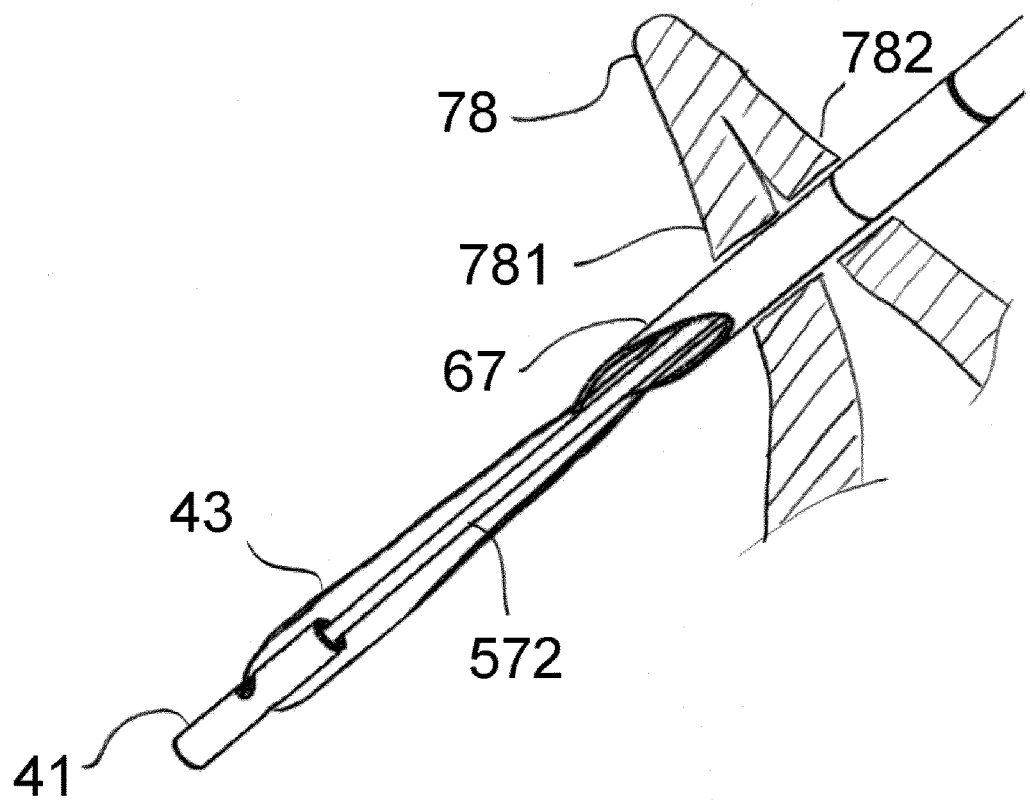
FIG. 7 represents a perspective view of the ejection of the distal anchor from the needle.

Inside the patient and referring to FIG. 7, a first tissue fold 78 is made according to known techniques, e.g. with the aid of an endoscopic assembly as described in WO 2015/052320. The needle 67 is then introduced transverse to the fold 78, to pierce both fold walls 781 and 782. When the needle arrives past distal fold wall 781, push rod 572 is pushed to eject distal anchor 41. Since proximal anchor 42 is loosely arranged over push rod 572, it will not be ejected and remains inside needle 67. Distal anchor 41 is left at the distal side of fold 78, and needle 67 is retracted from the fold 78 following push rod being retracted inside needle 67, without distal anchor 41 attached to it. As a result, distal anchor 41 is arranged at one side of the fold 78, and thread 43 forms a loop through distal anchor 41, through the fold 78 and into needle 67 where it is attached to proximal anchor 42. Tissue fold 78 can now be released.

It will be convenient to note that blind hole 413 is optional in distal anchor 41. Instead, bottom face 411 may be solid or closed to act as an abutting surface for push rod 572.

Figure 8:
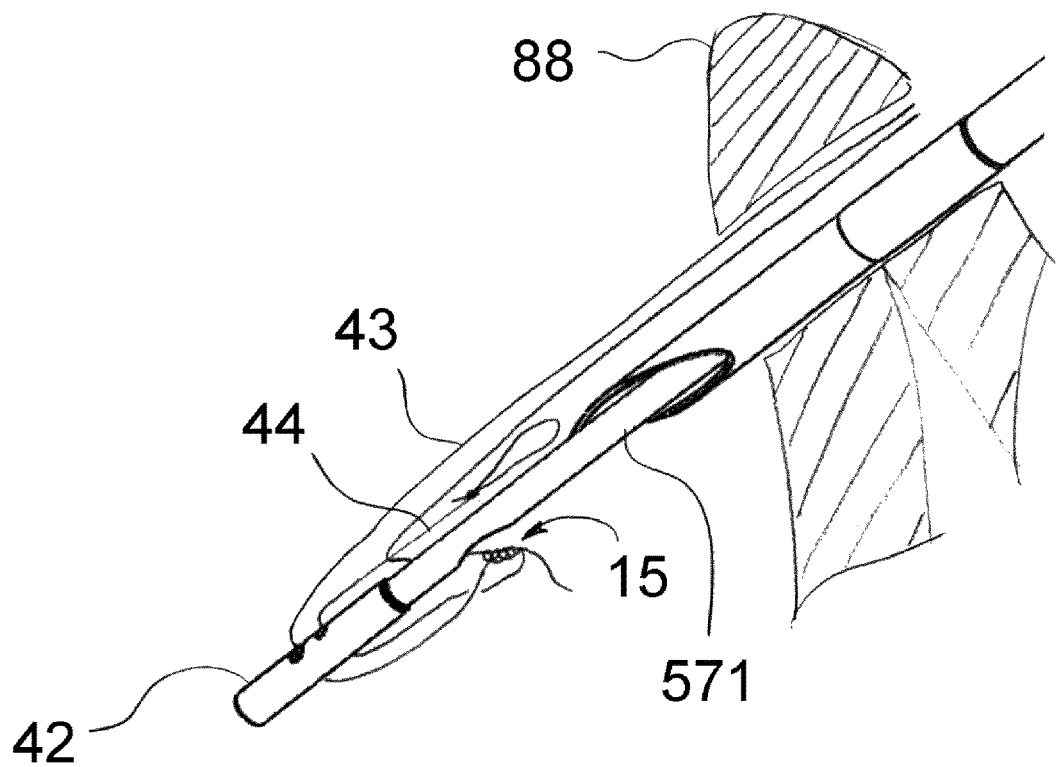
FIG. 8 represents a perspective view of the ejection of the proximal anchor from the needle.

In a next step of the procedure, referring to FIG. 8, a new tissue fold 88 may be made according to known procedures. Needle 67 pierces through tissue fold 88 to deliver proximal anchor 42 at the opposite side of the fold 88. Note that thread 43 will run from former fold 78, through the fold 88 along the outside of needle 67. Proximal anchor 42 is pushed out of needle 67 by push tube 571. Thereafter, push tube 571 is retracted inside needle 67 and needle 67 is retracted from fold 88, after which fold 88 may be released.

Figure 9:
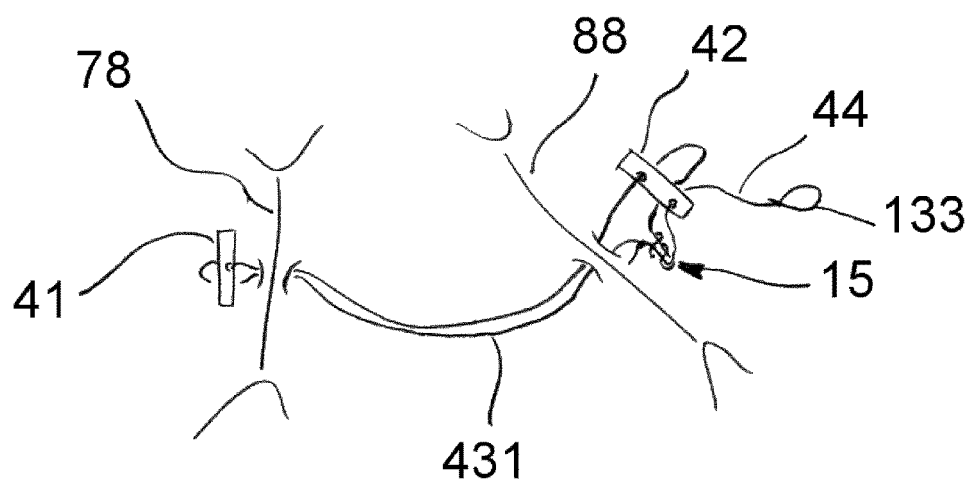
FIG. 9 represents a plan view of the introduction of the anchor assembly of FIG. 4 across a pair of tissue folds, prior to being tightened.

A result is obtained as shown in FIG. 9, with loop 431 of thread 43 extending between two tissue folds 78 and 88, which in turn are interposed between the two anchors 41 and 42. At this point, the anchor assembly 40 can be tightened in order to bring the folds 78 and 88 against each other to form a plication, which closes off a volume of endocavity interposed between the folds 78 and 88.

Figure 10:
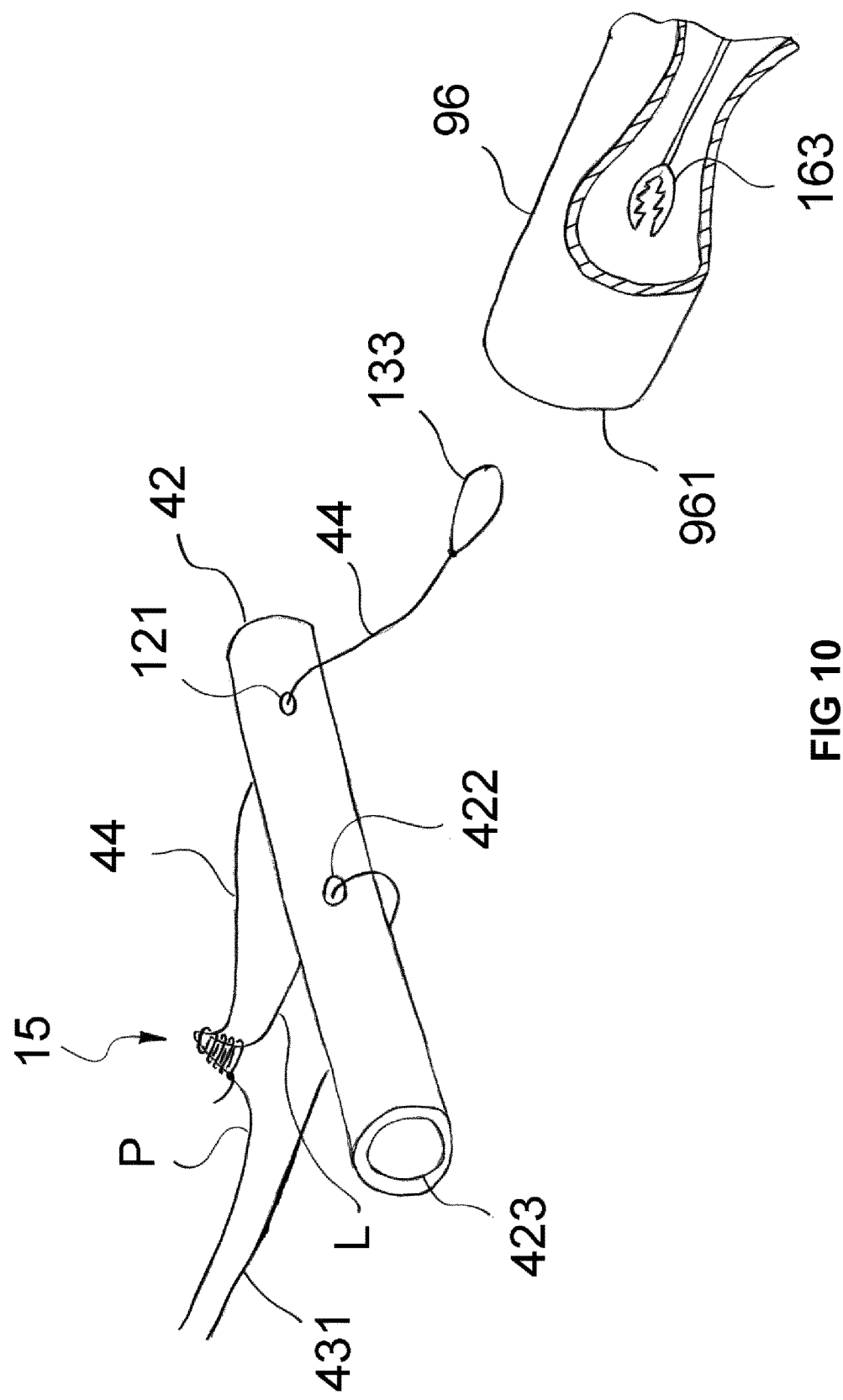
FIG. 10 represents a perspective view of a knot tightening assembly for use with the assembly of FIG. 4 or FIG. 3.

To tighten assembly 40, referring to FIG. 10, a push tube 96 is drawn into the endocavity. Push tube 96 is similar to knot tightening instrument 16, except that no slit 162 needs to be provided on push tube 96. A gripper or grasper 163 is slidingly arranged inside push tube 96 and is pushed out of tube 96 for grasping loop 133 arranged at the free end 44 of post limb. Once grasper 163 has grasped loop 133, it is retracted inside push tube 96 and the tube 96 is brought into abutment against proximal anchor 42, and positioned around through hole 121. At this position, post limb P can easily be pulled into push tube 96. This will draw sliding knot 15 against anchor 42 at the distal side of the anchor (opposite tube 96). Since sliding knot cannot pass through hole 121', it is retained by anchor 42 at the distal side thereof. Anchor 42, in co-operation with push tube 96, therefore acts as a knot retainer, allowing grasper 163 to further pull thread 44 and tighten the thread loop 43 between anchors 41 and 42. Once the folds 78 and 88 have been brought together, and desired tension is applied on the thread 43 in loop 431, grasper 163 can simply release loop 133, which will make thread free end 44 fall out of tube 96, from its distal end 961. Since both limbs of sliding knot 15 are under tension, the knot is secured and cannot slide back along free thread end 44. Therefore, the knot will maintain the loop 431 under tension.

The free thread end 44 can be left inside the patient or be cut away and extracted.

The tightening procedure can easily be followed through an endoscope camera and it will be clear that the surgeon may have the proximal side of the anchor 42, the distal end 961 of push tube 96 and a tiny part of knot 15 on image. Importantly, if anchor 42 starts twisting, this can be seen on camera. Furthermore, the ability of tightening the anchor assembly is not hindered in such case, since the push tube 96 will maintain itself around hole 121 due to the thread 44 passing through it. This avoids the formation of any undesired additional knots.

It will be convenient to note that the assembly 30 can be tightened following a same procedure as above.

Figure 17:
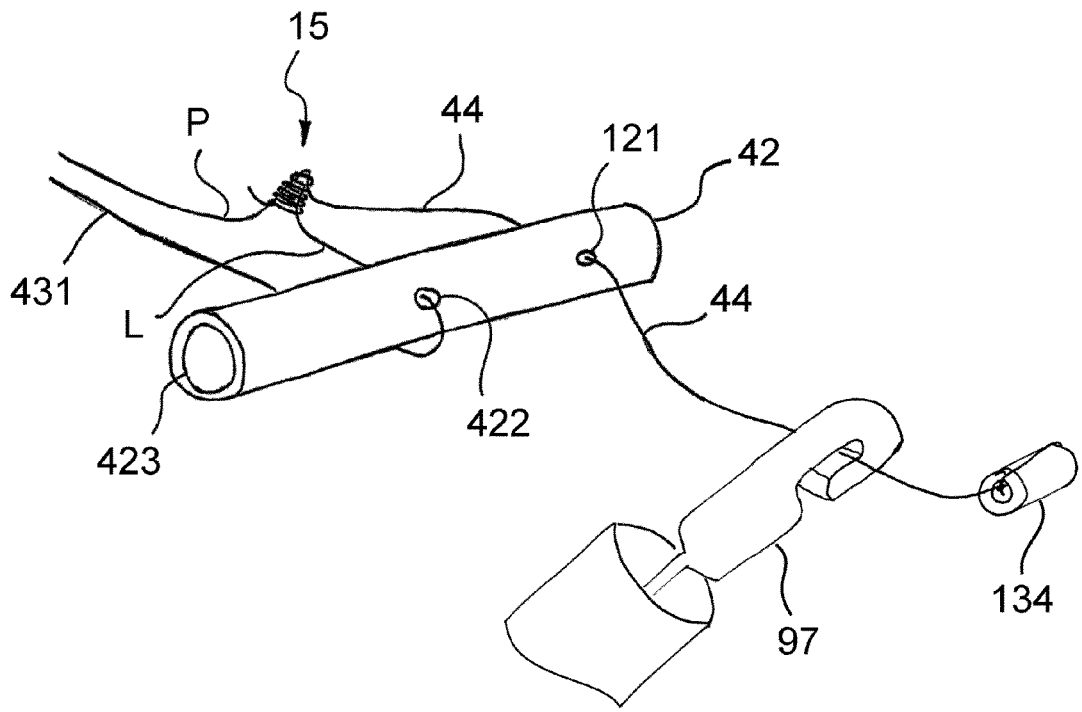
FIGS. 17-19 represent details of a proximal part of an anchor assembly, which differs from the assembly of FIG. 4 only in that the thread loop at the free end of the post limb has been replaced by hook or grasper retaining tags.
Figure 18:
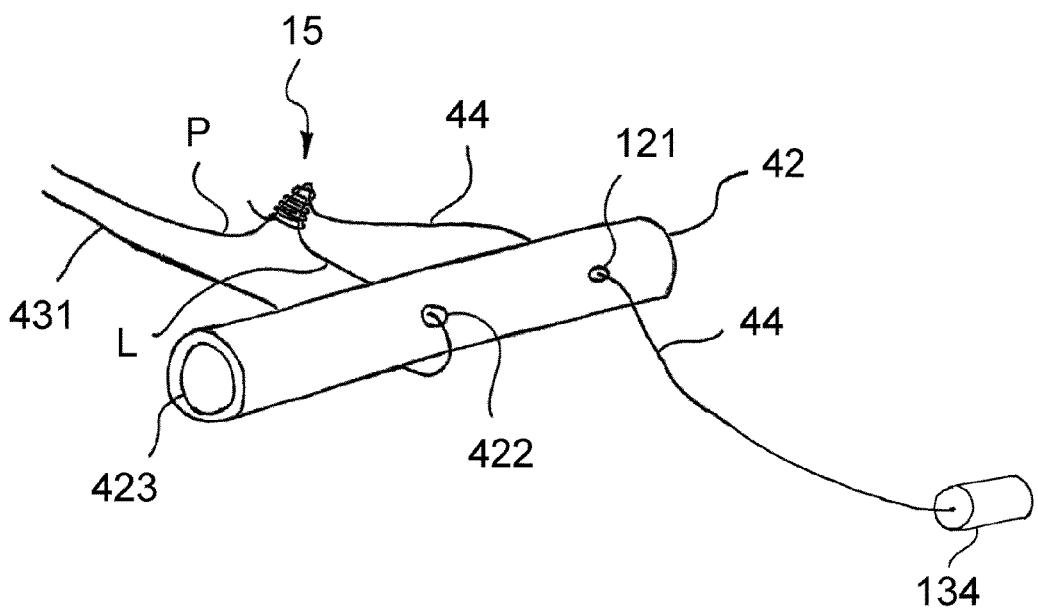
Figure 19:
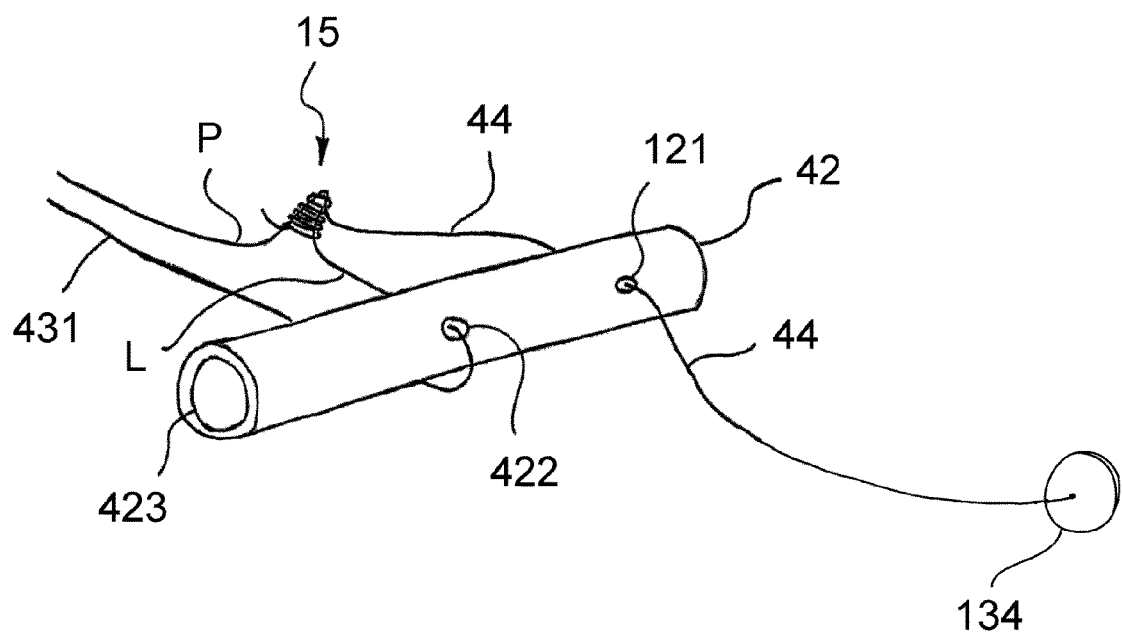

Referring to FIGS. 17-19, it may be advantageous to replace the thread loop 133 as in FIG. 4 by other grasper engaging means. The thread loop 133 can be replaced by a tag 134 at the extremity of the post limb's free end 44. The tag 134 provides for a thickened end part of the suture thread 44, having a diameter larger than the through hole 121. As shown in FIG. 17, this may facilitate engaging the suture thread with a hook instrument 97 or other grasper, for pulling on the slip knot 15. The tag 134 may also improve visibility of the post limb's free end. The tag 134 may have any suitable shape, such as a sleeve as shown in FIG. 17, with the post limb 44 forming a loop around the tag 134 for attachment, rod like as shown in FIG. 18, disc shaped as shown in FIG. 19. The tag can be moulded over the suture thread or be attached otherwise to it, such as by tying or gluing.

Advantageous aspects of anchor assemblies of the invention will now be described with reference to FIGS. 11-16. FIGS. 11-14 show an anchor placement situation possible with prior art anchor assemblies, such as the ones described above, whereas FIGS. 15 and 16 show an anchor placement situation possible with assemblies according to the present invention, in particular assembly 40.

Figure 11:
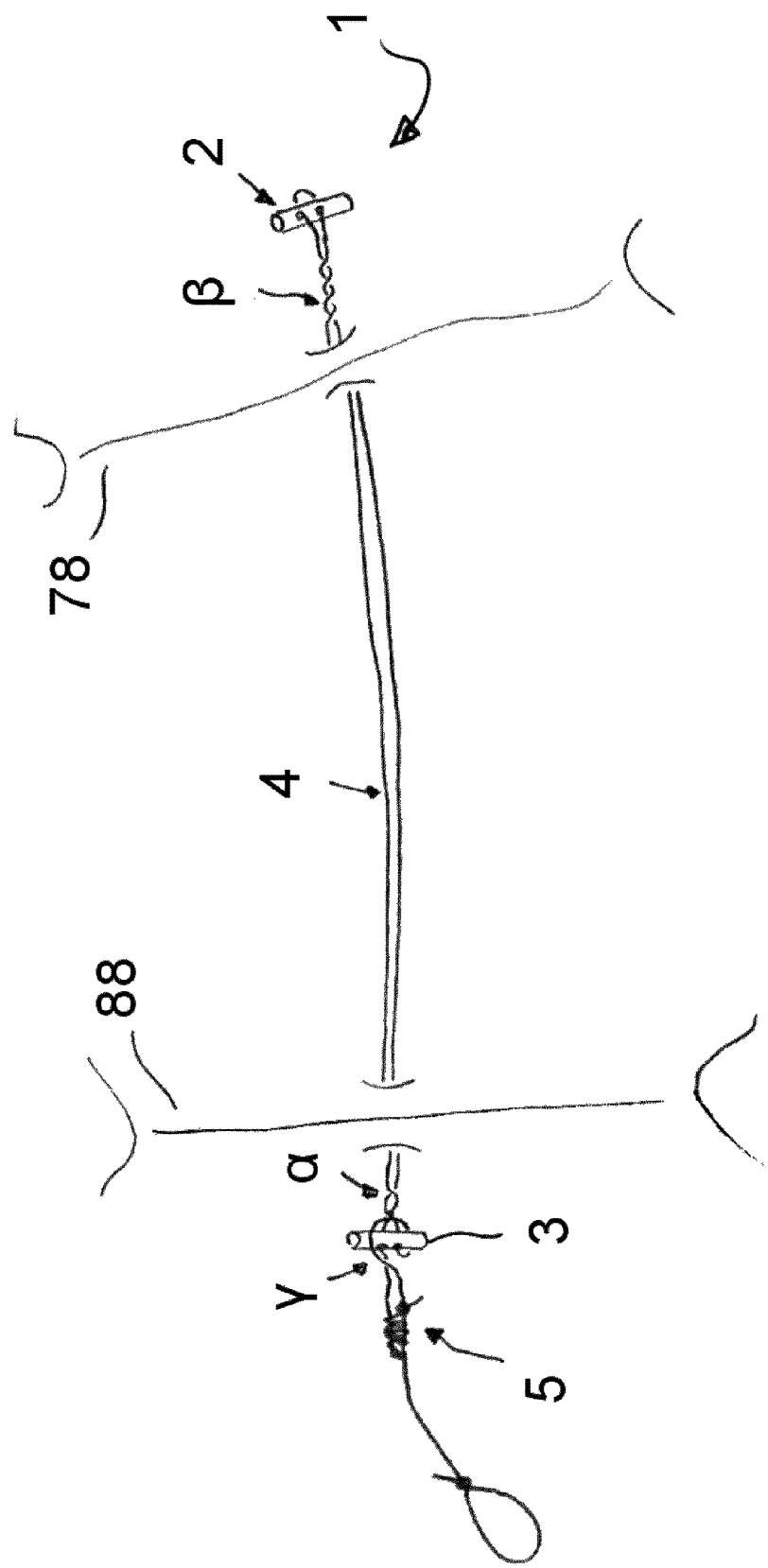
FIG. 11 represents a plan view of a prior art anchor assembly inserted through two tissue folds, depicting issues encountered with prior art anchor systems.

FIG. 11 shows a prior art assembly 1 with a pair of dual hole anchors 2, 3 connected through a thread loop 4 which passes twice through each anchor 2, 3. Loop 4 is closed by a knot 5 arranged proximally of the proximal anchor 3. Due to the fact that loop 4 passes through two holes in anchor 3, knot 5 is maintained proximally of the anchor 3 and cannot slide between the anchors 2 and 3. Assembly 1 is placed on two tissue folds 78, 88 as described above in relation to FIG. 9. This can be performed with a same endoscopic needle as described.

A twisting β of loop threads can readily occur when delivering the distal anchor 2 out of the needle. Loading the thread 4 and anchors 2, 3 in the needle results in unavoidable tensions that are partially released when delivering the distal anchor 2. The anchor hence tends to rotate around a transverse axis, perpendicular to its longitudinal axis, which causes the loop threads to turn with the anchor resulting in twisting β. Whilst retracting the needle through the tissue and moving to the other fold, typically little to no twisting occurs, as shown in FIG. 11. However, a same kind of twisting typically occurs when delivering the proximal anchor 3, even though this twisting α is generally less pronounced.

Figure 12:
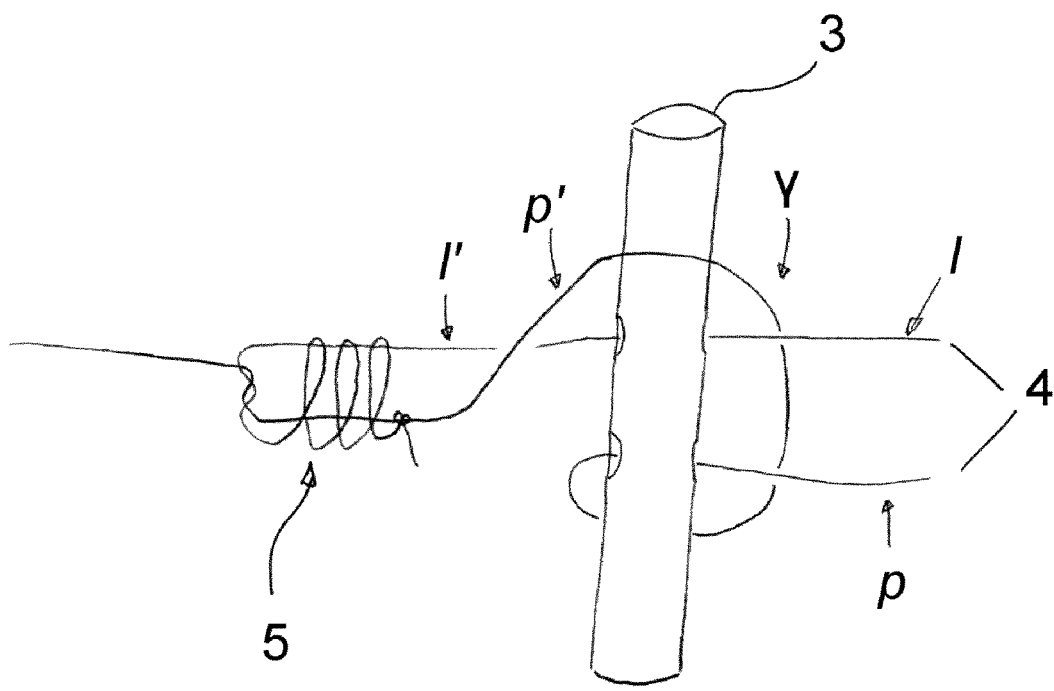
FIGS. 12 and 13 represent respectively a detail of the proximal and the distal part of the assembly of FIG. 11.

Another kind of twisting γ frequently occurs as shown in FIG. 11. This can happen at the release of the proximal anchor, or during tightening, when the anchor is not maintained relative to the knot. A closer view of that situation is shown in FIG. 12. As the proximal anchor 3 can initially be quite distant from the knot 5, the limbs p' and l' proximal of the anchor 3 can twist with the limbs p and l distal of the anchor 3, resulting in a situation as depicted in FIG. 12. It is even possible that the anchor 3 gets involved in the twisting. All this can lead to excessive friction when pulling the post p', or even the formation of an undesired knot, preventing knot 5 to slide along the post and hence a proper apposition of the tissues.

Figure 13:
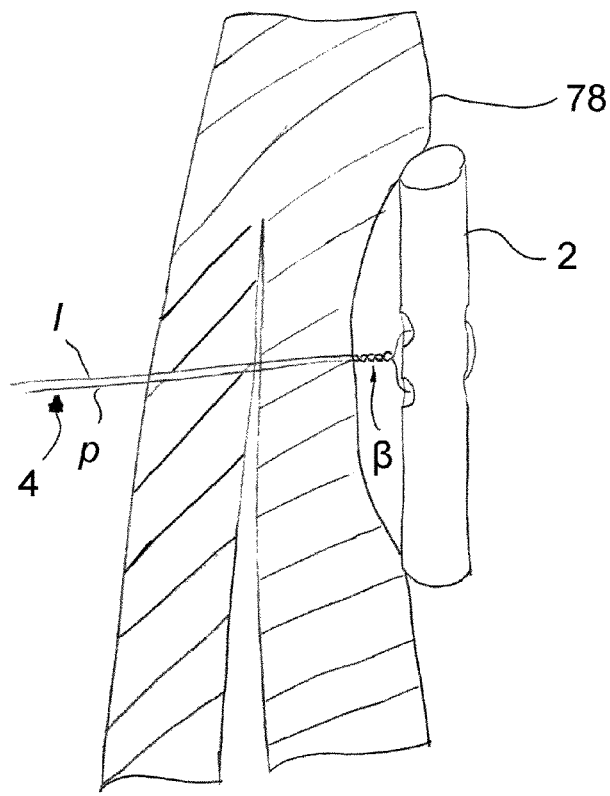

FIG. 13 depicts a detail of the distal arrangement with twisting β. The twisting does not generally pass through the tissue but is instead stuck up against the anchor 2. This generates too much friction for proper sliding of the thread limbs p and l. The distal anchor acts therefore as a locked backpack strap adjuster. Twisting cannot easily untangle as the anchor 2 is impacted on the tissue and does not rotate easily once the assembly 1 is being tightened.

Figure 14:
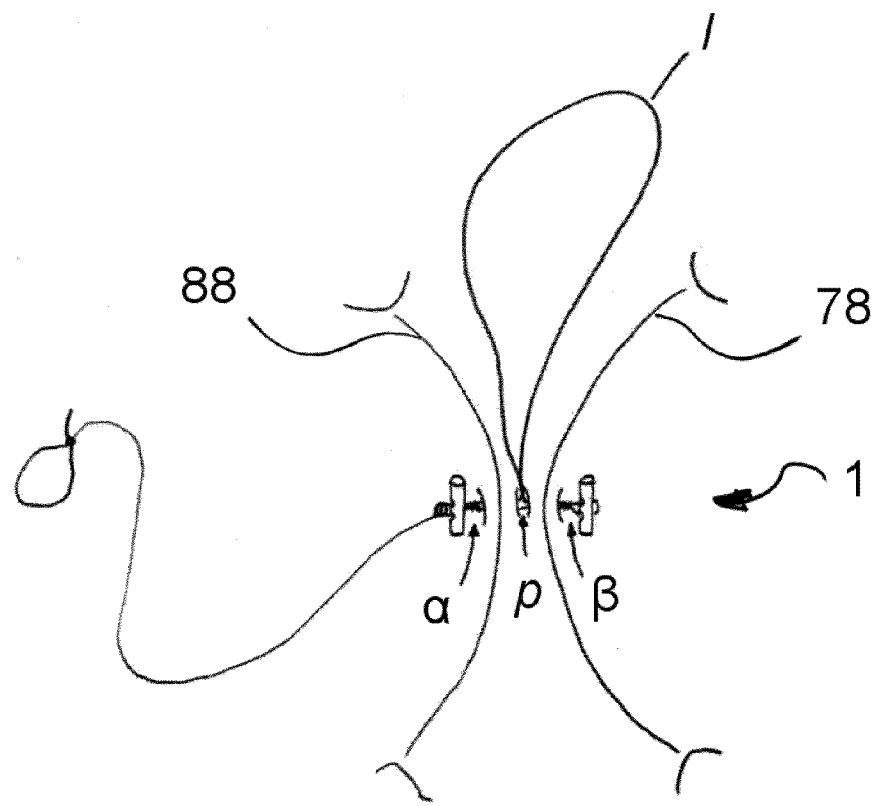
FIG. 14 represents the assembly of FIG. 11 after tightening.

FIG. 14 shows the resulting situation after tightening of assembly 1, when at least twisting β occurs. When tightening the knot 5 by pushing it along the thread limb p', limb p is shortened, but limb l cannot be shortened because anchor 2 is stuck along the loop 4 since twisting β makes anchor 2 act as a locked strap adjuster. As a result, limb l remains loose and does not contribute to the strength and tension of the anchor assembly. Although the tissue folds 78, 88 are tightened initially in this situation, two effects will lead to loosening of the apposition over time. First, as the loop limb l is not under proper tension, the knot securement is drastically reduced and the knot will gradually slide backwards (proximally). Second, with the repeated contractions of the organ, such as the stomach, the thread limbs p, l will gradually slide through twisting β, so that the two limbs p and l of loop 4 will even, loosening the apposition. In such a situation, twisting α and γ, if present, do not much prevent sliding of p and l through β.

Figure 16:
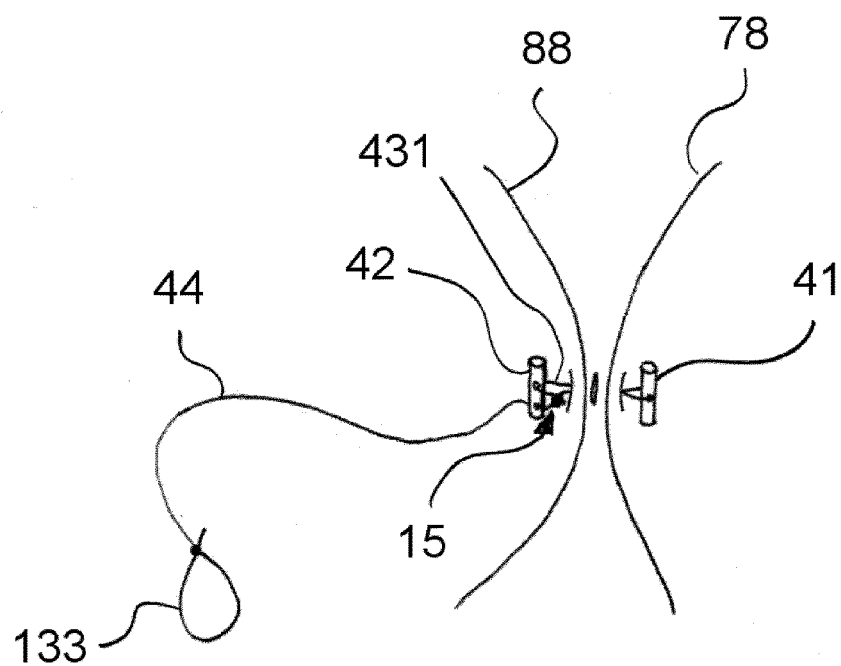
FIG. 16 represents the same view once tightened.
Figure 15:
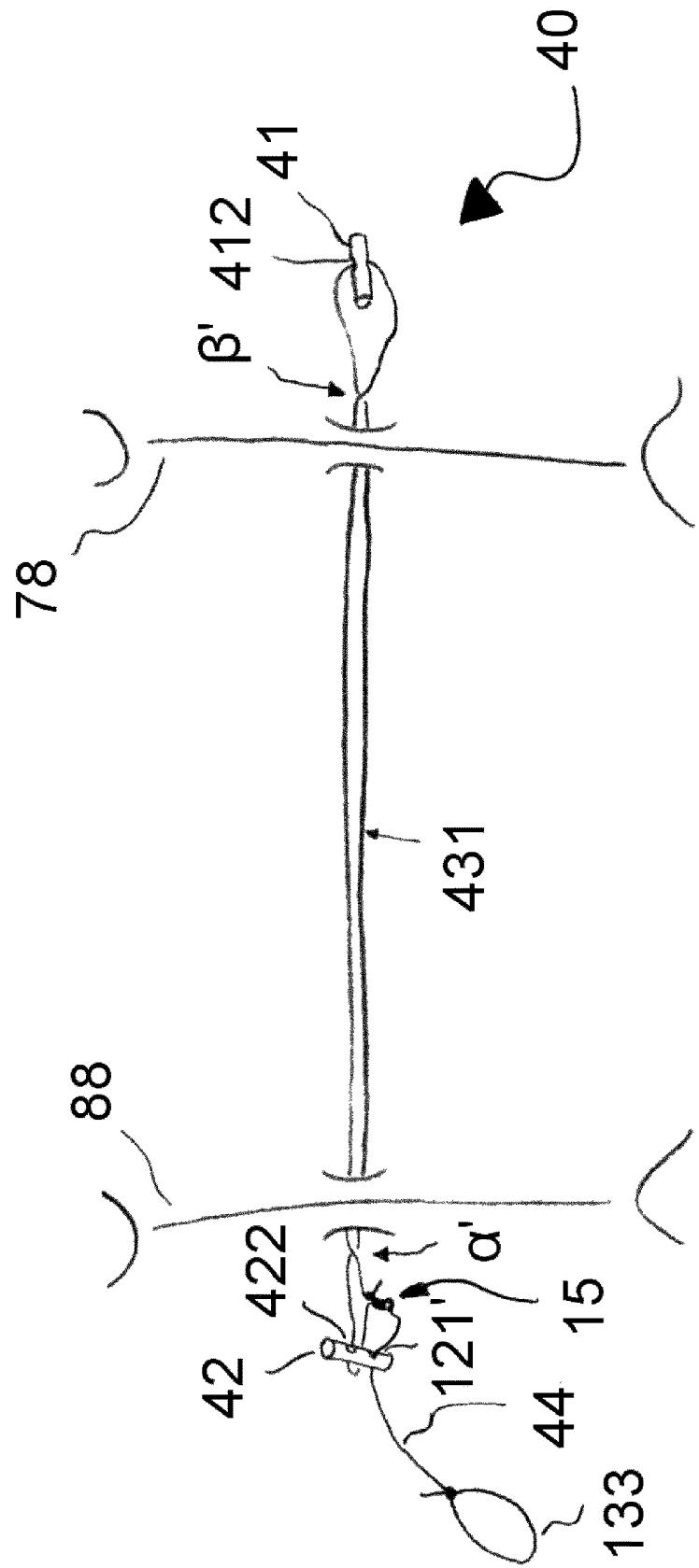

Conversely, the situation with assembly 40 according to aspects of the invention is shown in FIGS. 15 and 16. FIG. 15 shows assembly 40 after having been placed on the two tissue folds 78, 88. A twisting β' can occur as well on the distal side, but is less pronounced as the anchor 41 can easily pivot on the thread 43 without twisting the latter. Moreover, as the thread passes only once through the anchor, this geometry opposes less friction to sliding. On the proximal side, a twisting α' can also occur but again is less pronounced. However, no situation similar to twisting γ can occur here. Moreover, as the knot 15 abuts against the proximal anchor 42 whilst tightening, and the proximal anchor is maintained against the end 961 of the push tube 96, additional twisting on that side will not occur. FIG. 16 depicts the situation after tightening. It will be clear that a high reliability in securement of assembly 40 is obtained.

Similar conclusions can be drawn with assemblies 10 and 30. Since the thread limbs 13, 14 do not form a loop, twisting β and α cannot occur. Furthermore, twisting γ cannot occur either for same reasons as explained above.

Additional anchors can be placed in the loop 431, between the distal and proximal anchors, in order to tighten more than two folds together.

As they are being used in endoscopic surgery, in particular gastrointestinal endoscopic surgery, anchors according to aspects of the invention typically have a diameter between 0.5 and 1.5 mm in order to be able to be inserted in a needle of reasonable diameter. Anchors typically will have a length between 5 and 15 mm in order to provide sufficient anchoring surface. Threads for use in stomach reduction will have a diameter between 0.1 and 0.5 mm and are advantageously multifilament threads. The sliding knot will generally have a size which is three to four times the thread diameter. In this regard, the through hole 121' through which the post free end 44 passes advantageously has a diameter of at most twice the diameter of the suture thread, advantageously at most 1.5 times the diameter. Hence, the through hole 121', and possibly also through hole 121, advantageously has a diameter of 0.7 mm or less, advantageously 0.5 mm or less, advantageously 0.3 mm or less.

The invention claimed is:

1. An assembly for endoscopically securing gastrointestinal tissue folds, comprising:
   a first tissue anchor;
   a second tissue anchor;
   a first suture thread part and a second suture thread part, each of the first suture thread part and the second suture thread part having a secured end and a free end opposite the secured end;
   wherein the first suture thread part and the second suture thread part are connected to each other via a sliding knot, such that the first suture thread part forms a post of the sliding knot along which the sliding knot is arranged to slide during tightening of the assembly and such that the second suture thread part wraps around the post to create the sliding knot;
   wherein the assembly is configured to be tightened by sliding the sliding knot along the post;
   wherein the first suture thread part extends from the first tissue anchor past the sliding knot where the free end of the first suture thread part forms a post free end, and the second suture thread part extends from the second tissue anchor past the sliding knot where the free end of the second suture thread part is free, such that the sliding knot is interposed between the first tissue anchor and the second tissue anchor,
   the second tissue anchor further comprising a first through hole; and
   the post free end being configured to slide through the first through hole, the first through hole having a size preventing the sliding knot from passing through the first through hole, such that the second tissue anchor is configured to act as a knot retainer during tightening.

2. The assembly of claim 1, wherein the secured end of the first suture thread part and the secured end of the second suture thread part are attached to each other to form a thread loop which is closed by the sliding knot, wherein the thread loop slides through the first tissue anchor and the second tissue anchor such that the first tissue anchor and the second tissue anchor are configured to pivot on the thread loop without twisting the thread loop.

3. The assembly of claim 2, wherein the first tissue anchor further comprises a second through hole through which the thread, loop passes, and wherein the thread loop passes only once through the first tissue anchor.

4. The assembly of claim 2, wherein the second tissue anchor further comprises a third through hole through which the thread loop passes, and wherein the thread loop passes only once through the second tissue anchor.

5. The assembly of claim 4, wherein the second suture thread part, which wraps the post of the sliding knot, passes through the second tissue anchor.

6. The assembly of claim 4, wherein the first suture thread part, which forms the post of the sliding knot, passes through the second tissue anchor.

7. The assembly of claim 1, wherein the secured end of the first suture thread part is secured to the first tissue anchor and the secured end of the second suture thread part is secured to the second tissue anchor.

8. The assembly of claim 1, wherein the first through hole extends substantially along a direction of extension of the first suture thread between the first tissue anchor and the sliding knot.

9. The assembly of claim 1, wherein the post free end comprises a loop or tag for pulling the post relative to the sliding knot.

10. The assembly of claim 1, wherein at least one of the first tissue anchor and the second tissue anchor is elongate and of tubular shape.

11. The assembly of claim 1, wherein the sliding knot allows unidirectional movement along the post as the second suture thread part is maintained under tension.

12. The assembly of claim 1, comprising a push tube and a push rod slidingly receivable in the push tube, wherein at least one of the first tissue anchor and the second tissue anchor comprises an axial lumen of a size to freely slide the at least one of the first tissue anchor and second tissue anchor over the push rod, and wherein the at least one of the first tissue anchor and second tissue anchor has a size for abutting against a distal end of the push tube, and wherein the push tube and the first tissue anchor and the second tissue anchor are slidingly receivable in an endoscopic needle.

13. The assembly of claim 12, further comprising the endoscopic needle.

14. The assembly of claim 12, wherein the other one of the at least one of the first tissue anchor and the second tissue anchor is formed for abutting engagement against the push rod when the assembly is received in the endoscopic needle.

15. An assembly for endoscopically securing gastrointestinal tissue folds, comprising:
   a first tissue anchor;
   a second tissue anchor;
   a first suture thread part and a second suture thread part, each of the first suture thread part and second suture thread part having a secured end and a free end opposite the secured end;
   wherein the first suture thread part and the second suture thread part are connected to each other via a sliding knot, such that the first suture thread part forms a post of the sliding knot along which the sliding knot is arranged to slide during tightening of the assembly and such that the second suture thread part wraps around the post to create the sliding knot;
   wherein the assembly is configured to be tightened by sliding the sliding knot along the post;
   wherein the first suture thread part extends from the first tissue anchor past the sliding knot where the free end of the first suture thread part forms a post free end, and the second suture thread part extends from the second tissue anchor past the sliding knot where the free end of the second suture thread part is free, such that the sliding knot is interposed between the first tissue anchor and the second tissue anchor;

the first tissue anchor further comprising a first through hole; and the post free end being configured to slide through the first through hole, and the first through hole having a size preventing the sliding knot from passing through the first through hole.

16. The assembly of claim 15, wherein the secured end of the first suture thread part and the secured end of the second suture thread part are attached to each other to form a thread loop which is closed by the sliding knot, wherein the thread loop slides through the first tissue anchor and the second tissue anchor such that the first tissue anchor and the second tissue anchor are configured to pivot on the thread loop without twisting the thread loop.

17. The assembly of claim 16, wherein the first tissue anchor comprises a second through hole through which the thread loop passes, and wherein the thread loop passes only once through the first tissue anchor.

18. The assembly of claim 16, wherein the second tissue anchor comprises a third through hole through which the thread loop passes, and wherein the thread loop passes only once through the second tissue anchor.

* * * * *